United States Patent [19]
Weill et al.

[11] Patent Number: 5,496,524
[45] Date of Patent: Mar. 5, 1996

[54] REACTOR FOR THE THERMAL CONVERSION OF METHANE

[75] Inventors: Jérome Weill, Lyons; Laure Capogna, Saint Denis; Véronique Arrondel, Houilles; Jean-Jack Boumendil, La Colle sur Loup, all of France

[73] Assignees: Institut Francais du Petrole, Rueil Malmaison; Electricite de France, Paris Cedex; Gaz de France, Paris, all of France

[21] Appl. No.: 293,270

[22] Filed: Aug. 19, 1994

Related U.S. Application Data

[62] Division of Ser. No. 962,453, Oct. 19, 1992, Pat. No. 5,365,005.

[30] Foreign Application Priority Data

Oct. 17, 1991 [FR] France .................... 91 12948

[51] Int. Cl.⁶ .................... B01J 19/24; C07C 2/00
[52] U.S. Cl. .................... 422/199; 422/200; 422/240; 585/500
[58] Field of Search .................... 585/500, 415, 585/913, 921, 943; 422/199, 200, 240; 219/85, 10.81

[56] References Cited

U.S. PATENT DOCUMENTS

| | | | |
|---|---|---|---|
| 4,007,015 | 2/1977 | Barber | 422/199 |
| 4,057,396 | 11/1977 | Matovich | 422/199 |
| 4,135,881 | 1/1979 | Baky et al. | 422/199 |
| 4,926,001 | 5/1990 | Alagy et al. | 585/500 |
| 5,008,091 | 4/1991 | Bassi et al. | 423/245.1 |
| 5,113,032 | 5/1992 | Cameron | 585/500 |
| 5,160,501 | 11/1992 | Alagy et al. | 585/500 |
| 5,270,016 | 12/1993 | Alagy et al. | 422/199 |
| 5,365,005 | 11/1994 | Weill et al. | 585/500 |

FOREIGN PATENT DOCUMENTS 0323287  7/1989  France .

Primary Examiner—Robert J. Warden
Assistant Examiner—N. Bhat
Attorney, Agent, or Firm—Millen, White, Zelano & Branigan

[57] ABSTRACT

An apparatus for the thermal conversion of methane into hydrocarbons of higher molecular weight, comprising a reactor (1) of elongate form, connected on the one hand, at a first end, to an inlet for supplying gaseous mixture containing methane (process gas) and on the other, at the opposite end, to an outlet (10), the reactor comprising on the first end side a plurality of elements disposed in at least two layers disposed between two refractory walls, at least one refractory wall being disposed between the outside walls of the reactor, the layers being substantially parallel to the axis of the reactor, at least one of these layers comprising a series of sheaths (4) inside which there are electric heaters (3) which thus form a layer of heating elements, the elements being disposed in such a way as to define spaces or passages for the circulation of gaseous mixtures and/or effluents, the heaters and the sheaths being adapted to heat the said passages by successive independent cross-sections substantially at right-angles to the axis of the reactor, each cross-section comprising at least one transverse row of elements.

8 Claims, 3 Drawing Sheets

REACTOR FOR THE THERMAL CONVERSION OF METHANE

This is a division of application Ser. No. 07/962,453 filed Oct. 19, 1192, now U.S. Pat. No. 5,365,005 issued Nov. 15, 1994.

BACKGROUND OF THE INVENTION

The invention relates to a process for the thermal conversion of methane into hydrocarbons of higher molecular weight and the apparatus for carrying out the said process. More particularly, it relates to a process for the thermal conversion or cracking of the methane in a reactor comprising electric heating means and, by dehydrogenation thermal coupling of this molecule, permitting the production principally of acetylene, ethylene, benzene and a little coke. Any methane sources well known to a man skilled in the art may be used. Natural gas may cited as a highly current source of methane. A non-exhaustive list of these sources is provided for instance in European Patent Application EP-A-323287 in the name of the Institut Françcais du Pétrole, one of the assignees of this invention. In the majority of cases, the gas containing methane which is introduced into the reactor contains from 1 to 90% and sometimes even more of at least one other gas.

In European Patent Application EP-A-323287, there is described a process for the thermal conversion of methane into hydrocarbons of higher molecular weight, comprising electric heating means with a transfer of heat to the gaseous mixture containing the methane to be converted, through seal-tight walls of sheaths of ceramic material which insulate the said heating means from the gaseous mixture containing the methane. In this process, the heating zone is heated by a supply of electrical energy by means of electric resistors and the heat released by Joule's effect in these resistors is transmitted mainly by radiation to the sheaths of ceramic material disposed around resistors in a non-contiguous manner. The gaseous feeds which circulate substantially at right-angles to the axis of the heated sheaths are heated substantially by convection and by radiation. In the performance of this process, two spaces are defined within the reactor:

- on the one hand, the reaction space or process space outside the sheaths protecting the resistors, in which the gaseous mixture containing methane circulates,
- on the other hand, the resister space formed by the volume comprised between the actual resistors and the insulating sheaths into which preferably an inert gas, that is to say a gas containing no methane or any hydrocarbon capable of a thermal conversion reaction or any compound capable of reacting violently with methane or hydrogen, is introduced. This gas is likewise chosen in such a way that it does not damage the resistors used and does not cause accelerated ageing of the resistors.

One of the greatest problems when carrying out the thermal conversion of methane is linked with coke formation. Indeed, if it forms in too great a quantity, it is likely to damage the furnace before the decoking operations can be performed and furthermore, from the economic point of view, its formation represents a substantial loss forth with regard to the electrical energy consumed ant the methane consumed in forming the coke. This problem, well known to a man skilled in the art, is partly resolved by the introduction into the gaseous mixture containing the methane to be converted of a quantity of hydrogen representing from 1 to 90% by volume in relation to the total volume of gas. In spite of this precaution, coke formation has not been completely eradicated, mainly at the level of the walls of the sheaths and on the other surfaces which are at elevated temperature and which are in contact with the gaseous mixture containing the methane.

This explains why, in carrying out the methane conversion process in an electrically heated pyrolysis furnaces, it is desirable:

- to have a relatively large quantity of hydrogen present in the process zone,
- to provide electrical resistors capable of delivering at high temperature a considerable quantity of energy per unit of surface area and per unit of time,
- to have conditions conducive to satisfactory heat transfer so that the temperature of the heating elements (that is to say the temperature of the surface of the sheaths in contact with the gaseous mixture containing methane) is not too much greater than the temperature desired for carrying out conversion of the methane.

In carrying out the process, it has been stipulated that it is preferable for the resistor space to be filled by a gaseous medium such as nitrogen, carbon dioxide or air. The use of air is only conceivable if the seal provided by the sheaths between the process space and the resistor space is perfect. Indeed, there would otherwise be a substantial risk of forming a gaseous mixture at a very high temperature, comprising oxygen, methane and hydrogen, which therefore entails a risk of explosion. The provision of a completely seal tight system is relatively difficult and furthermore requires the use of ceramic material which offers a very high level of seal-tightness and which is therefore of very high quality, that is to say a ceramic material the density of which is close to theoretical density and which is free from open pores.

The use of such a ceramic material is extremely expensive, which penalizes the process. Therefore, one is induced to accepting the use of sheaths of less than perfect seal-tightness and to use either nitrogen with the not inconsiderable risk, in view of the resistor skin temperature, of the formation (in the case of silicon carbide resistors) of silicon nitride, which in principle has no effect on the mechanical strength of the resistors but does cause a fluctuation in the resistivity of these resistors and therefore accelerates their ageing, the more so the higher the temperature of the resistor (and therefore of the heating element) and the greater the amount of energy provided by the resistor, or to use carbon dioxide gas which, even if the rate of leakage from the resistor space into the process space is minimal, will inevitably cause problems at the stage involving separation of the products formed during the course of thermal conversion of the methane, complicating this stage on the one hand by their presence and on the other by the presence of carbon monoxide and water which will inevitably form by reaction between the carbon dioxide, the methane, the coke and the hydrogen in the process space.

SUMMARY OF THE INVENTION

One of the objects of the invention is to remedy the aforedescribed drawbacks. The objects which it is aimed to achieve and which meet the problems raised by the prior art are essentially the following:

- to minimize coke formation, particularly on hot surfaces such as for example the walls of sheaths enclosing the resistors, to use as a gas in the resistor space a gas or a mixture of gases preferably comprising a gas already present in the gaseous mixture circulating in the process space, which makes it possible to use sheaths which do not possess a very high level of seal-tightness, to improve heat exchange between the gaseous mixture containing the methane and the hot surfaces in contact with this mixture, to minimize the problems of distribution of the gases inside the reactor, to enhance the viability of the apparatus and its ease of construction and dismantling for decoking and maintenance of the reactor.

The present invention relates to a process and an apparatus for carrying out the process, which provide notable improvements compared with prior art constructions and processes such as for example easier, more flexible and better controlled performance and lower costs both at investment level and also in respect of utilities.

More particularly, the invention relates to a process for the thermal conversion of methane into hydrocarbons of higher molecular weight in a reaction zone which is elongate in one direction, comprising a heating zone a cooling zone following the said heating zone and in which the effluents from the heating zone are cooled, a gaseous mixture containing methane being caused to circulate in the said heating zone in a direction of flow which is substantially parallel with the direction of the reaction zone, characterized in that the said heating zone comprises between two walls of refractory material, at least one longitudinal zone in which the said gaseous mixture circulates, the said longitudinal zone comprising a plurality of elements disposed in at least two layers which are substantially parallel inter se and substantially parallel with the direction of the reaction zone, the said elements forming in transverse projection a cluster of triangular, square or rectangular pitch, at least one of these layers comprising a series of sheaths inside which there are electric heating means, so forming a layer of heating elements, the said heating means thus being insulated from direct contact with the gaseous mixture containing the methane and the said heating elements being grouped in successive transverse sections each comprising at least one transverse row of elements, the said sections being perpendicular to the direction of the reaction zone, independent of one another and supplied with electrical energy in such a way as to define at least two parts in the heating zone, the first part making it possible to raise the charge to a temperature at least equal to approx. 1500° C. and the second part, following on from the first part, making it possible to maintain the charge at a temperature substantially equal to the maximum temperature to which it was raised in the first part, and according to which the effluent from the heating zone is cooled by introduction into the cooling zone of a cooling fluid after which the said hydrocarbons of higher molecular weight are collected at the end of the reaction zone.

The heating zone is heated by the supply of electrical energy through heating means such as electrical resistors; the heat given off by Joule's effect in these resistors is transmitted mainly by radiation to the sheaths disposed around the resistances in a non-contiguous manner. These sheaths are usually of ceramic material or some other refractory material which can withstand the required temperatures and the reducing and oxidizing atmospheres of the medium such as for example certain new metal alloys from KANTHAL SA such as KANTHAL AF or KANTHAL APM, or even of refractory cement. These sheaths may be porous or not. It is often easier and less expensive to use porous sheaths which allow a gaseous mixture to pass from the resistor space to the process space. The gaseous mixture containing methane which circulates in the heating zone in a direction which is substantially perpendicular to the axis of the sheaths is essentially heated by convection and radiation.

The thermal dehydrogenation of the methane is a highly endothermal reaction and means that a quite substantial density of heat flow must be obtained at a high level of temperature, of around 1100° to 1500° C. It is necessary that the maximum contribution of heat be made in the zone where the endothermal cracking and dehydrogenation reactions are performed; furthermore, having regard to the reactivity of the products formed, such as acetylene or ethylene, it is necessary to have a relatively short controlled contact time followed by a rapid quenching in order to obtain a temperature profile of the "square" type and in order to avoid excessive coking.

Heat exchanges are one of the key elements for this type of highly endothermal reaction where it is necessary to transfer quite substantial amounts of energy from the resistors to the gaseous mixture containing methane and hereinafter referred to as the process gas. During a preliminary study carried out of heat exchanges in a pyrolysis furnace constructed according to the model used in the present invention, it was noted that the exchange of heat from the resistance to the sheath is an essentially radiative exchange but on the other hand there is virtually no radiative exchange between the sheath and the process gas. Indeed, this latter is normally essentially constituted by a hydrogen-methane mixture, a mixture which absorbs virtually no or very little radiation emitted by the sheaths. The transfer of heat between the process gas and the sheaths is therefore in the case in question in the present invention essentially a transfer by convection. In such a case, the quality of the heat exchanges will be linked directly to the surface area available for the exchange and to the surface area/volume ratio.

Thus, if the surface area for exchange is relatively small, it will be necessary, in order to obtain a given process gas temperature corresponding to a previously chosen conversion level, to increase the temperature of the sheaths in proportions which will be greater as the surface area becomes smaller, which implies an increased risk of coke formation and also the need to raise the temperature of the resistors, which causes a more rapid ageing of these resistors or even if the previously chosen rate of conversion is very high, the quantity of energy to be transferred becomes very great and the risk of the resistors deteriorating is quite considerably aggravated.

The walls play an important part in heat exchange since they are capable of absorbing the rays emitted by the sheaths; consequently the temperatures of sheaths and of the walls have a tendency to balance. It is then possible to increase considerably the surface area available for exchange by modifying the design of the device as follows: whereas in the initial conception, the sheaths protecting the resistors and making it possible for the transfer of heat to the process gas were preferably arranged in quincunx, according to the present invention they will more often than not be aligned which makes it possible to make up n rows or layers of m resistors in the longitudinal direction (for a total number of resistors equal to n×m) and in a preferred embodiment it will be possible to associate a certain number of preferably aligned pseudo heating elements which makes it possible to constitute z rows or layers of y pseudo heating elements (for a total number of pseudo heating elements equal to z×y), which means that at least one longitudinal zone and more often than not at least two longitudinal zones will be formed, each comprising at least two layers of elements of which at least one comprises heating elements, each zone being separated from the next by a wall of refractory material. By radiation, the temperature of these walls increases and has a tendency to attain the same level as that of the sheaths enclosing the resistors. These walls will therefore likewise participate in the heating of the process gas by convection and the same will apply to the pseudo heating elements if these are provided. Thus, in this embodiment, as the heat exchange area is substantially increased, it will be possible to obtain the same process gas temperature with a relatively lower sheath and wall temperature, which consequently makes for a reduction in coke formation. In the present description, the term heating element designates the assembly constituted by a protective sheath and at least one resistor inside the said sheath, and the term pseudo heating element denotes an element of a refractory material usually of the same height as the heating element and of which the cross-section more often than not has the same form and the same surface area as those of heating elements or a similar form or a derived form and a different surface area. For example, if the heating elements have a circular cross-section, the pseudo heating elements may have a cross-section which is circular, semi-circular or which corresponds to a quarter of a circle.

In this embodiment, convective exchanges between the process gas and the walls are generously enhanced and may be still further improved by imparting considerable velocities to the gas and by creating zones of turbulence. Increasing the velocity of the gases may be achieved for example by using walls the shape of which is favourable to this increase in velocity and the formation of turbulent zones. Walls of particular forms are shown in FIG. 1A, by way of non-restrictive examples. The walls and the pseudo heating elements are normally of a refractory material. Any refractory material may be used for producing the walls and these pseudo elements and by way of non-limitative example, zirconium, silicon carbide, mullite and various refractory cements may be cited. In a preferred embodiment, the heating elements will comprise a sheath of a ceramic material.

In view of the fact that it is by no means indispensable to have a tight seal at the level of the walls, since the composition of the gas is virtually identical on each side of the walls, this embodiment requires a minimal increase in the cost of the furnace. Indeed, on the one hand it is not necessary to have especially thick walls nor for their construction to be particularly complex, but on the other hand the overall dimensions of the furnace do increase very much because essentially the width of the furnace is due to the width of the sheaths. By way of example, the sheaths may have a width of around 150 mm for a wall thickness having a width of around 50 mm, which only means an increase in the width of the furnace of less than about 30%. Moreover, it is preferably for each wall to comprise at least one means of permitting the pressures situated in the longitudinal zones on either side of the wall to be balanced. By way of example of a simple but effective means which makes it possible to balance the pressures, it is possible to quote the creation of zones comprising one or a plurality of perforations or porous zones.

An additional advantage of this embodiment comprising walls is that of allowing simpler construction of the furnace, the vertical walls not only improving the transfer of heat by convection but making it possible to support the roof of the furnace. It should be noted that according to the preferred embodiment of the invention, the pseudo heating elements likewise improve the transfer of heat and likewise participate in supporting the furnace roof.

According to one of the characteristic features of the invention, the electrical resistors which supply heat to the heating zone are independently supplied with electrical energy either individually or in transverse rows or even in small groups, in order to define heating sections along the heating zone and in order thus to be able to modulate the quantity of energy provided throughout the length of this zone. The heating zone is normally composed of 2 to 20 heating sections and preferably 5 to 12 sections. In the first part of this zone, the gaseous mixture containing methane, previously heated to approx. 750° C., is normally raised to a temperature which is at most equal to approx. 1500° C. and advantageously between 1000° and 1300° C. (the start of the heating zone is situated at the place where the charge is introduced).

These heating sections are modulated in a conventional manner; the heating elements corresponding to the aforesaid sections are generally supplied by thyristor modulator assemblies. Transformers make it possible if necessary to adapt the voltages a priori while the modulators permit of fine and continuous adjustment of the injected power.

In order to allow the assembly to be regulated, each heating section may be provided with an insertion pyrometer with a thermocouple suitable for the temperature level involved; these pyrometers are disposed in the spaces in which the charge circulates the data are transmitted to the controller which operates the thyristor modulator.

In the first part of the heating zone, the electrical energy serves almost exclusively to raise the reaction mixture from its initial temperature (for example approx. 750° C.) to the temperature at which the endothermal dehydrogenating coupling reactions of the methane occur (for example approx. 1200° C.). It is therefore at the commencement of the second part of the heating zone that it is necessary to provide maximum energy to the reaction environment, which is easily achieved for instance by modulation of one or more heating sections and/or by using modules (described hereinafter) for manufacturing the furnace, comprising a different number of pseudo elements according to whether they are situated at the start of the first part of the heating zone or towards the middle or the end of this zone and similarly according to their position in the second part of the heating zone.

The length of the first part of the heating zone normally represents from 20 to 80% of the total length of the heating zone, advantageously from 30 to 70%. The electrical energy supplied to this first of the heating zone is such that it generates a considerable temperature gradient, normally from approx. 0.5 to approx. 25° C./cm and advantageously approx. 1 to approx. 20° C./cm.

In the second part of the heating zone, the electrical energy provided to the various heating sections of this zone is modulated in such a way that the fluctuation in temperature along this zone is minor, usually less than approx. 50° C. (+or −25° C. around the desired value) and advantageously less than approx. 20° C. Furthermore, the use of different transverse heating sections (for example as well as the use of different modules comprising a greater or lesser number of pseudo heating elements) which are independent of one another makes it possible, at the level of the second part of the heating zone, to apply maximum heat energy at the place where the major part of the endothermal reactions takes place while maintaining a virtually uniform temperature in the rest of the heating zone.

The length of the heating zone is usually approx. 50 to approx. 90% of the total length of the reaction zone.

Particularly under the above-described heating conditions, a quite substantial heat flow is achieved at an elevated temperature level. This normally entails a particular choice for the material used for the resistors which, in addition to being resistant to the atmosphere in which the resistors are immersed under operating temperature conditions, have to be capable of delivering a relatively substantial output per unit of surface area. As an example of a material which can be used for making resistors, it is possible to quote silicon carbide, boron nitride, silicon nitride and molybdenum bisilicide ($MoSi_2$). Usually, it is preferable to use molybdenum bisilicide resistors which offer numerous advantages when they are used at high temperature:

they accept a considerable charge (power emitted per unit of surface area) which may be as much as 20 $W/cm^2$, they can work at a very high temperature they display negligible ageing in course of time, they readily withstand reducing atmospheres at elevated temperatures. In the process according to the invention, the heating zone is followed by a cooling (or quenching) zone in order very rapidly to reduce the temperature of the effluent from the zone to approx. 300° C. for example.

According to an embodiment, direct quenching is carried out; the reaction effluent leaves the heating zone and is very rapidly cooled by being brought directly into contact with a cooling medium which is injected into the effluent by means of at least one injector, normally of a ceramic material, disposed at the periphery of the reactor. As a cooling medium, it is possible to use gases of liquefied petroleum, propane, hydrocarbon oils or water. Propane is the preferred quenching gas because it can also be partially cracked and so contribute to the formation of products such as ethylene. The total effluent resulting from the mixture is then collected and separated.

In accordance with a preferred embodiment, the reaction effluent emanating from the heating zone is cooled by being brought into indirect contact with a cooling medium, for example by causing the said medium to circulate through seal-tight ducts inside the cooling zone. All these characteristic features, by virtue of this process, make it possible to achieve a thermal conversion of the methane into acetylene, ethylene and benzene products which is achieved with a good rate of conversion and considerable selectivity of these products.

The hydrocarbon feeds which can be used within the framework of the invention are gaseous charges under normal temperature and pressure conditions, usually comprising a percentage by volume of methane of at least 10%, for example from 10 to 99%, and more often than not from 20 to 99% and preferably from 30 to 80%. As stipulated hereinabove, the rest of the batch in almost all cases comprises a proportion of hydrogen by volume which ranges most often from 1 to 90%. It may likewise comprise other gases such as for instance aliphatic hydrocarbons, saturated or otherwise, comprising a number of atoms equal to or greater than 2 such as ethylene, ethane, propane or propylene. It may also contain nitrogen, carbon dioxide or carbon monoxide.

While remaining within the framework of the invention, it is possible to add dilution steam to charges defined hereinabove; the ratio by weight of dilution steam to hydrocarbon charge is generally around 0.1:1 to 1:1.

The charges to be treated have a dwell time in the reaction zone which is normally approx. 2 milliseconds to approx. 1 second and preferably of approx. 30 to approx. 400 milliseconds. As a sealing gas, that is to say as a gas which is introduced into the resistor space (this space is that which was defined hereinabove in connection with the analysis of the European Patent Application EP-A-323287), and preference will be given to a gas which will make it possible to obtain the longest effective life of the resistors while entailing, due to the leakage of the said gas into the process space, a minimum of complications concerning the reaction itself (minimum coke formation) and also the separation of the products downstream of the reactor, sometimes referred to as a pyrolysis furnace. For example, it is possible to choose as a sealing gas nitrogen, $CO_2$, hydrogen or a mixture of 2 or more of these gases. It is likewise possible to use as a sealing gas one of the gases mentioned hereinabove containing water vapour. Usually it is preferred to introduce into the sheaths enclosing the resistors a gas containing hydrogen. This gas may be substantially pure hydrogen, industrial hydrogen or a mixture of hydrogen with another inert gas such as for example nitrogen, helium, argon, steam or $CO_2$ gas. Preferably, pure or industrial hydrogen or a mixture of helium and hydrogen or a mixture of argon and hydrogen or a mixture of water vapor and hydrogen is used which normally contains at least 5% and preferably at least 10% by volume of hydrogen. When a mixture of nitrogen and hydrogen is used, this usually contains at least 25% and preferably at least 50% by volume of hydrogen.

In a preferred embodiment, the electric heating means will be insulated from direct contact with the gaseous mixture containing methane by sheaths into which a gas containing hydrogen is introduced, the said sheaths being of suitable permeability and the gas being introduced into the interior of the sheaths being at such a pressure that there is at least at certain points a diffusion of at least a part of the hydrogen contained in the gas introduced into the resistor space, towards the process space, that is to say from the interior of the said sheaths to the outside of the said sheaths, this hydrogen possibly being diluted then in the gaseous mixture containing the methane.

It would not be a departure from the scope of the invention if the permeability of the sheaths were such that it allowed the diffusion of all the gaseous compounds contained in the gas introduced into the resistor space towards the process space. This permeability may result from a seal on each sheath, provided voluntarily in an incomplete way and/or the use of a material constituting the sheaths which has an open porosity allowing the hydrogen to pass through, that is to say in other words a material which is permeable to hydrogen. More often than not, it is recommended to use a permeable material.

Thus, in accordance with a preferred embodiment of the invention, the sheaths insulating the electric heating means from direct contact with the gaseous mixture containing the methane are made from a porous material of sufficient porosity to allow the hydrogen to diffuse through the said sheaths. Thus, these sheaths are preferably made from a porous ceramic material having an open porosity of at least approx. 1% and of at most approx. 40% by volume in proportion to the volume of the wall of the sheath and usually of approx. 5% to approx. 30%.

The use of substantially pure hydrogen which diffuses at least partly towards the process space has a number of advantages. It does not complicate the separations downstream of the pyrolysis furnace because the gas to be cracked is normally a mixture of methane or natural gas and hydrogen in a proportion by volume of preferably 10 to 80% hydrogen and most frequently 30 to 70%.

The introduction of hydrogen along the pyrolysis furnace makes it possible to reduce the overall size of the furnace.

Indeed, if a certain proportion of hydrogen in the cracked gas is intended, then at the intake to the furnace the proportion will be reduced and for one and the same dwell time to be respected, the reaction volume will be less, therefore the size of the furnace will also be reduced. But, moreover, this embodiment will result in an increasing proportion of hydrogen along the pyrolysis furnace, which represents an advantage from the point of view of the kinetics of cracking and the stability of the products because at the beginning of the furnace, too great a quantity of hydrogen would excessively inhibit the cracking reactions, but at the end of the furnace, when there is a substantial quantity of formed products, particularly ethylene and acetylene, it is advantageous to have a greater quantity of hydrogen in order to avoid coke formation. The desired effect will indeed be achieved if there is hydrogen penetrating the process zone at the level of each seal (at least one per sheath) on each sheath protecting the resistors and/or through the wall of the sheaths by diffusion.

Furthermore, in accordance with a preferred embodiment of the process of the present invention, in view of the fact that it is not indispensable to seek the most perfect seals possibly between the process space and the resistor space, the cost of production of the furnace is reduced by likewise reducing the thermo-mechanical stresses at the level of the sheath flanges, which enhances the viability of the apparatus as a whole. Another advantage resides in choice which it is then possible to make with regard to the sheaths protecting the resistors, dividing the process space from the resistor space. Indeed, when nitrogen or $CO_2$ is used as the sealing gas, it is necessary for many reasons to limit the consumption of this gas, that is to say the leakage of the said gas from the resistor space into the process space. This is normally achieved by seeking as perfect a seal-tightness as possible, particularly at the point where the sheaths are joined to the rest of the furnace. This is also achieved by using ceramic sheaths, particularly sheaths of silicon carbide which are as seal-tight as possible, that is to say of very good quality and therefore very expensive.

It is indeed well known to a man skilled in the art that there are many varieties of ceramic material and in particular silicon carbide, which originate from vastly differing qualities of constituent powder and sintering conditions. Without wishing to go into detail, however, it may be noted that one of the quality criteria is linked to the least possible porosity remaining after sintering. It is well known that if a part of this porosity is found to be closed, that is to say has no effect on the overall seal-tightness of the material, another and not inconsiderable part, above all for the most ordinary silicon carbide, is an open porosity and that in particular there is at high temperature a diffusion of the hydrogen through this material. It will therefore be readily understood that when a gas such as nitrogen or $CO_2$ is used as the sealing gas, a very high quality silicon carbide has to be used which has a density close to theoretical density, in other words free from any open pores, in order to avoid firstly a leakage of the said gas from the resistor zone into the process zone and secondly as the partial pressure differential of the hydrogen is positive in the process-resistor sense, a diffusion of the hydrogen contained in the process gas towards the resistor space.

The use of sheaths made from ceramic material, particularly silicon carbide of average quality, comprising open pores amounting to at least approx. 1% by volume (for example approx. 20% by volume) is thus not only possible but even desirable, which reduces the cost of producing the furnace. Furthermore, the very existence of this open porosity creates on the surface of the ceramic sheath, on the process space side, a partial hydrogen pressure which to a certain extent insulates the surface of the ceramic from the process gas which, without wishing to be bound by any theory, explains the substantial reduction in coke formation since this latter normally forms mainly on the surface of the sheaths, the products formed being in contrast in a local atmosphere which is richer in hydrogen and therefore less favourable to coke formation.

The term 'open porosity' in the description of the present invention relates to the porosity constituted by microcavities included in the solid ceramic parts in question, the adjective 'open' signifying that there is freedom of passage on the one hand between the majority of the said microcavities and on the other between the said microcavities and the inner and outer surfaces of the parts in question; the idea of free passage must also be considered as a function of the nature of the environment and the physical conditions in which the ceramic is present. In particular, for small size molecules such as hydrogen or helium, free passage will be easy, the more so since if there is a difference in pressure between the two surfaces of the ceramic part. In this case, the part is said to be permeable, to hydrogen for example, or is not fluid-tight. In the description of the present invention, the term 'closed porosity' refers to the porosity consisting of microcavities which do not communicate with the surface of the part. In that case, this closed porosity only results in an overall diminution of the density of the part.

Another object of the invention is the apparatus for carrying out the process. This apparatus may likewise be used for carrying out other endothermal reactions which normally occur at temperatures above approx. 600° C. and for example approx. 700° to approx. 1450° C., with dwell times amounting to 2 milliseconds up to a few seconds, for example up to 20 seconds.

More particularly, the invention relates to an apparatus for carrying out the process and which comprises a reactor (1) of elongate form according to an axis of preferably square or rectangular cross-section, comprising at a first end means of supplying a gaseous mixture and at the opposite end means of discharging the effluent produced and, between these two ends, means of supplying a cooling medium, characterised in that the said reactor comprises in a first part (the same side as the first end) at least one longitudinal zone between two walls of refractory material, which are substantially parallel with each other and substantially parallel with the axis of the reactor, the said longitudinal zone comprising a plurality of elements, disposed in at least two layers, substantially parallel inter se and substantially parallel to the axis of the reactor, at least one of these layers comprising a series of sheaths (4) inside which there are electric heating means (3) which thus form a layer of heating elements, the said elements being disposed in such a way as to define between them and/or between the layers which they form and/or between them and the walls of the spaces or passages for circulation of the gaseous mixtures and/or effluents, the said heating means and the said sheaths being adapted to heat the said passages in successive independent transverse sections which are substantially at right-angles to the axis of the reactor, each transverse section comprising at least one transverse row of elements while the said reactor comprises in addition means for the automatic control and modulation of the heating and which are connected to the said heating means, and comprising in a second part (8) (the side of the opposite end) contiguous to the first part, means (9) of cooling the effluent and connected to the said cooling medium supply means.

According to a preferred embodiment, the said apparatus will comprise means of introducing, at a suitable pressure, a gas containing hydrogen into the interior of the sheaths (4) and the said sheaths will be sheaths of sufficient permeability that, at least at certain points, at least a part of the hydrogen is allowed to diffuse from the interior of the said sheaths to the exterior of the said sheaths, this hydrogen then becoming diluted in the said gaseous mixture.

The means of introducing the gas at a suitable are those known to a man skilled in the art. They may moreover comprise means of regulating and monitoring the pressures prevailing inside and outside the said sheaths. The said cooling means are means adapted to cool the effluent leaving the first zone, by direct or by indirect contact.

The sheaths enclosing to resistors, normally in a non-contiguous fashion, may be disposed in a superposed arrangement or in quincunx and may in a transverse projection form a cluster with a triangular, square or rectangular configuration.

The total number of layers comprising heating means and the number of heating means in each sheath and per layer are not decisive in the process; obviously, they are a function of the dimensions of the heating means, the sheaths which enclose them and the walls separating the longitudinal zones. The heating elements may be identical to one another or different, both in their dimensions and in their heating output. By way of example, a heating element may comprise from 1 to 5 and more frequently from 1 to 3 resistors inside the sheath.

The number of heating elements determines the maximum electric power available for a given reaction volume, and similarly has its effect on the dwell time of the charge; it will be chosen as as function of the rate of flow of charge admissible, taking these parameters into account.

Within the framework of the present invention, it is possible to construct the whole of the reactor, heating zone and quenching zone, either in monobloc form, or even by the juxtaposition—contiguous or otherwise—of various modules, more often than not of identical form, which are assembled to one another by any usable means, for example with the aid of flanges. For example, the reactor may comprise at least two longitudinal zones formed by the juxtaposition in the longitudinal sense and in the transverse sense of a series of modules each comprising at least one longitudinal wall of refractory material. In a preferred embodiment, each wall of refractory material separating two adjacent longitudinal zones comprises at least one means permitting the balancing of pressures between the two zones. When the reactor is formed by the association of modules, these latter will preferably be assembled in a non-sealing-tight fashion, so that gases are able to pass from one longitudinal zone to the longitudinal zone situated on the other side of the wall, at the point of assembly. The reactor normally comprises from 1 to 20 and preferably from 2 to 8 longitudinal zones. One of the advantages of producing the furnace by the association of consecutive modules resides in the unity which is derived therefrom. For example, it is possible to associate with each module one furnace roof element and also one heating and power control unit, the module then constituting a heating section. Furthermore, dismantling and maintenance of the furnace are simplified as a result. According to another embodiment, a plurality of modules may be associated in order to form a heating section. It is likewise possible to install the various modules in the furnace comprising walls, continuous or otherwise, which have been previously positioned. The electric heating means which can be used within the framework of the present invention are preferably heating resistors the constituent material of which must be resistant to the atmosphere in which they are immersed. In a preferred embodiment, resistors are used which are produced from a material which will withstand an overall reducing atmosphere, up to temperatures of the order of 1500° C.; it is preferable to use resistors of molybdenum bisilicide, for example hair-pin shaped resistors. The elements present in each longitudinal zone are preferably substantially cylindrical or tubular elements, all of which have substantially the same outside diameter and substantially the same height, and in which those enclosing the heating means and forming a layer of heating elements are cylindrical or tubular sheaths having an inside diameter D of approx. 1.2 to approx. 8 times and more often than not approx. 1.5 to approx. 4 times the maximum diameter d of the circle embracing the said heating means and the other elements are hollow elements such as cylindrical or tubular sheaths or solid cylindrical elements.

These sheaths of refractory material are most frequently of a ceramic material. It is possible to use ceramics such as mullite, cordierite, silicon nitride, silicon carbide, silica or alumina; silicon carbide is the preferred material because it offers good heat conductivity. The longitudinal zones are separated by walls manufactured from a material which may be the same as that used for producing the sheaths but which is often different, particularly on grounds of furnace production cost. In a preferred embodiment of the reactor, each longitudinal zone is formed by the juxtaposition of a series of constituent modules of square or rectangular cross-section, each comprising at least two elements which form a transverse row, of which at least one is formed by a sheath (4) inside which there is an electric heating means (3), and constitutes a heating element (19), the said elements being disposed in such a way that they define between them and/or between them and the walls of the said zone, spaces or passages for the circulation of gaseous mixtures and/or effluents, and the said modules being juxtaposed in such a way that the elements form between two walls of refractory material, substantially parallel inter se and substantially parallel with the axis of the reactor, at least two layers which are substantially parallel inter se and substantially parallel with the axis of the reactor.

Each constituent module may comprise at least two transverse rows of two or three heating elements which are so disposed that the juxtaposition of these modules makes it possible to obtain at least two layers of heating elements, the said layers being perpendicular to the axis of the reactor and the said elements forming in transverse projection a cluster of triangular, square or rectangular configuration.

According to another embodiment, each constituent module may comprise at least two transverse rows of which at least one is formed by heating elements and of which at least one other, contiguous upon a row of heating elements, is formed by pseudo heating elements of a refractory material, the said elements being disposed in such a way that the juxtaposition of these modules makes it possible to obtain at least two layers of elements, the said layers being perpendicular to the axis of the reactor and the said elements forming in transverse projection a cluster of triangular, square or rectangular configuration. According to this last-mentioned embodiment, each constituent module may comprise on its periphery pseudo heating elements, the said pseudo heating elements having a cross-section such that by juxtaposition of the modules, those situated at the level of the edge at which the said modules are juxtaposed form pseudo elements of substantially the same cross-section as the heating elements, those contiguous upon one side having a cross-section which is less than the cross-section of the heating elements and preferably a cross-section equal to approx. half the cross-section of the said heating elements and equal to approx. one-quarter in the case of those which are contiguous upon two sides of the module.

The elements are disposed in parallel layers which are substantially perpendicular to the direction of flow of the process gas, preferably substantially aligned, so that the distance separating two adjacent elements is as small as possible while taking into account the vital factors of admissible loss of charge; the distance between the elements of two adjacent layers or the distance between the elements in one layer and the nearest wall is normally the same as that between two consecutive elements in a given layer.

This distance will normally be such that the passages formed between the elements or between the nearest wall, passages in which the gaseous mixture containing methane circulates, will measure approx. 1 to approx. 100 mm and most frequently approx. 5 to approx. 40 mm.

According to a particular embodiment of the invention, the free spaces or passages defined hereinabove intended for circulation of process gas, are at least partially occupied by linings, usually of ceramic material, which are preferably heat conductive. Thus, for a given type of reactor, it is possible to reduce the dwell time of the charge in this reactor while homogenising the flow of gaseous mixture and providing a better distribution of the dissipated heat. These linings may take various forms and may for example take the form of rings (Raschig rings, Lessing rings or Pall rings), saddles (Berl saddles), bars, closed cylindrical tubes.

BRIEF DESCRIPTION OF THE DRAWINGS

The invention will be more clearly understood from the description of some embodiments, given purely by way of illustration and implying no limitation, which will be given hereinafter and in which reference is made to the appended drawings in which similar parts are designated by the same reference letters and numerals. In the drawings.

DETAILED DESCRIPTION OF THE PREFERRED EMBODIMENTS

Figure 1A:
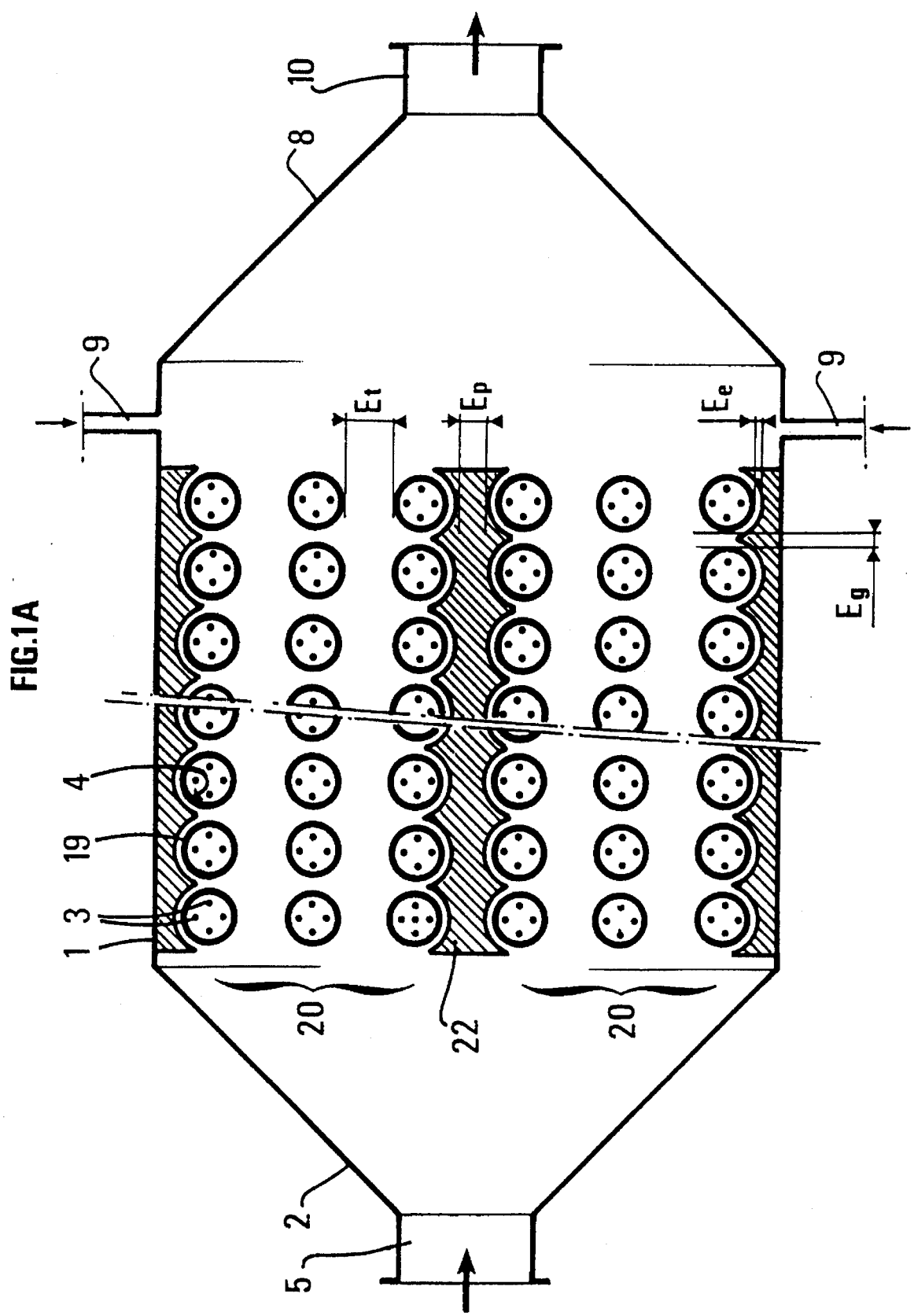
FIG. 1A shows a longitudinal section through a reactor, on a plane at right-angles to the axis of the elements. In the case of FIG. 1A, this reactor only comprises heating elements in the heating zone.

In accordance with one embodiment, FIG. 1A shows a substantially horizontal reactor (1) of elongate form and of rectangular cross-section, comprising a distributor (2) which makes it possible, through an inlet aperture (5), to supply the reactor with the gaseous mixture to be reacted. This gaseous mixture which contains for example 50% methane, has been preheated, preferably by convection, in a conventional preheating zone, not shown in the drawing. The reactor comprises two longitudinal zones (20) separated by a wall (22), ideally of a ceramic material, each wall having a plurality of heating elements (19), comprising electric heating elements (3) enclosed in sheaths (4) disposed in parallel layers and forming in one plane (the plane of the drawing) a cluster having a square configuration. These layers define transverse heating sections which are substantially perpendicular to the axis of the reactor defined according to direction of flow of the charge. Likewise, on its sides parallel with the direction of flow of the charge, this reactor has walls of a form which is adapted to create turbulence, comprising cells at the level of each element (19). The heating sections are supplied with electrical energy independently, thanks to a pair of electrodes (6a, 6b in FIG. 1C), pyrometric thermocouple probes (7 in FIGS. 1B and 1C) are housed in the spaces in which the charge circulates between the elements (19) and they make it possible automatically to regulate the temperature of each heating section by a conventional regulating and modulating device not shown in the drawings.

In the first part of the heating zone, the elements are heated in such a way that the temperature of the charge changes rapidly from 750° C. (preheating temperature) to approx. 1200° C.; this progressive heating zone generally represents about 65% of the total length of the heating zone; then, the gaseous mixture circulates in the second part of the heating zone in which the temperature is generally maintained at a constant level which is substantially equal to that attained at the end of the first heating zone, in other words generally 1200° C. approx. To this end, the electric power supplied to several heating sections which constitute the second part of the heating zone is modulated; thus it is possible to achieve a variation in temperature which does not exceed approx. 10° C. around the desired value. The length of this second heating zone represents approx. 35% of the total length of the heating zone.

At the outlet of the heating zone, the reaction effluent is cooled in a cooling zone (8). It comes in contact with a quenching agent such as propane, introduced via quenching injectors (9) disposed on the periphery of the reactor (1) and connected to an outside source of propane, not shown. All the effluent gas is cooled to a temperature of approximately 500° C. and collected by an outlet orifice (10) at the end of the reaction zone (1).

According to another embodiment, not shown, the effluent may be cooled by circulating through seal-tight ducts disposed in the zone (8) through which the quenching agent flows, these ducts being connected to the external source of quenching agent.

Figure 1B:
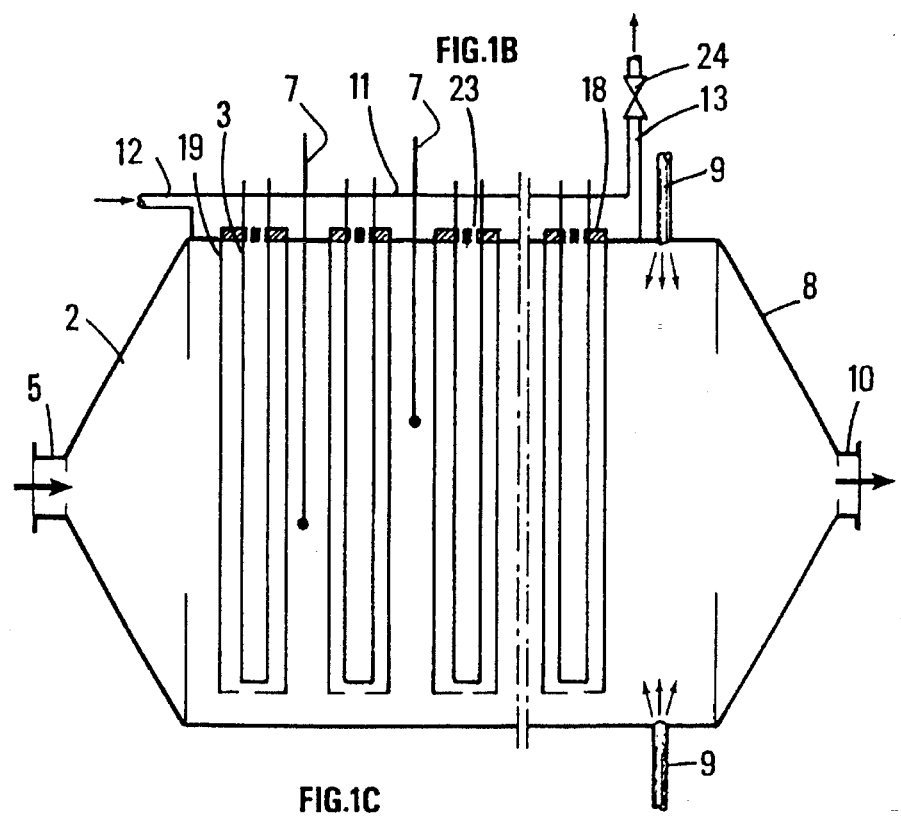
FIGS. 1B and 1C show a longitudinal section through a reactor taken on the axis of the elements.

FIG. 1B shows, for a horizontal reactor, the same elements as those described in connection with FIG. 1; in addition, a protective casing (11) is shown which comprises an aperture (12) through which is introduced the gas containing hydrogen and an aperture (13) provided with a valve (24) which makes it possible to regulate the flow of gas containing hydrogen. This casing (11) is fixed on the metal frame of the reactor (1) and encloses the heating elements, formed by the assembly of electrical resistors and sheaths containing them, except for the ends of the electrical resistors through which the electrical energy is supplied. The resistors (3), of hairpin shape, are positioned in the sheaths (4) by means of washers (18), of ceramic fibre for example, comprising passages (23) allowing the gas containing the hydrogen to enter the space comprised between the resistors and the sheaths.

Figure 1C:
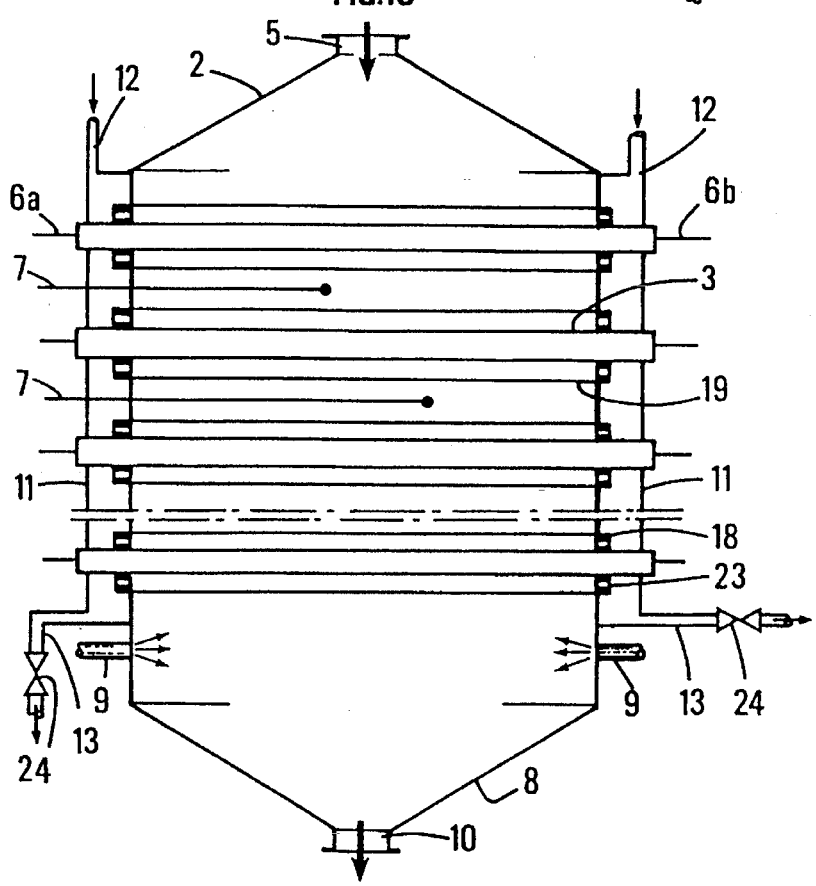

In accordance with the recommended embodiment, the reactor will comprise a casing (11) partitioned in such a way that transverse zones are defined each of which is separately supplied with a sealing gas. This embodiment makes it possible to limit the effect of the loss of charge of the reactor on the rate of leakage of sealing gas from the resistor space into process space and therefore permits of better control of this rate of leakage. For a vertical reactor, FIG. 1C shows the same elements as those described in connection with FIG.

1A; in addition, the drawing shows the protective casings (11) fitted with apertures (12) and (13) allowing circulation in the casings of the gas containing hydrogen which penetrates the resistor space through the apertures (23) in the washers (18) which assist with positioning of the resistors. The apertures (13) are fitted with valves (24) which allow easier control of the flow of hydrogen-bearing gas. The circulation of the gas containing the hydrogen is normally carried out in a slight over-pressure in relation to the pressure of the process gas inside the reactor, so ensuring a perfectly controlled atmosphere and a better diffusion into the process space of the hydrogen contained in the gas.

The pressure could be virtually equal to that of the process gas and in this case as in the case of an overall over-pressure, it is usually preferable for the partial pressure of the hydrogen to be slightly higher in the resistor space than in the process space in order to be certain that the hydrogen diffuses properly from the resistor space into the process space. The difference in the partial pressures of hydrogen will more often than not be such that the partial pressure of the hydrogen within the gas contained in the resistor space is at least 0.1% and preferably at least 1% greater than that of the hydrogen contained in the process gas. The difference in absolute pressure between the resistor space and the process space, or over-pressure, will preferably be such that the pressure in the resistor space is at least 0.1% and more often than not at least 1% greater than the pressure in the process space. It is not necessary to have a very high over-pressure and in most cases the pressure in the resistor space remains less than twice the pressure in the process space.

Figure 2:
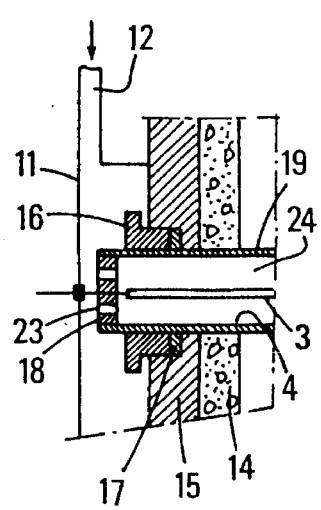
FIG. 2 illustrates a detail of the heating zone in a plane identical to that in FIGS. 1B and 1C.

FIG. 2 shows a detail of an embodiment of the heating zone according to the invention. As an electric heating means, resistors (3) of cylindrical shape are used. At each of their ends, these resistors have cold zones and a part of the central zone which is the hot zone for instance represents approx. 68% of the total length.

A reactor of rectangular cross-section is produced, its walls being constituted by insulating refractory cement (14) and a metallic framework (15). A circular hole is made in the two opposite lateral walls and through the holes is passed a sheath (4) of ceramic material for example, the diameter of which is twice that of the electrical resistor (3). The sheath (4) is positioned by means of a compression gland system (16) acting in a groove at the level of the metallic framework on a cord of refractory material (17), for a cord of ceramic material. The resistor (3) is positioned in the sheath (4) by means of washers (18), of ceramic fiber, for example, comprising orifices (23) to allow passage of the gas containing hydrogen and introduced into the casing (11) via the duct (12) and into the resistor space (34).

The hot zone of the resistor (3) is so positioned that it does not penetrate the throughway passing through the insulating concrete wall. It is not vital to use a cord (17) at the compression gland level since within the framework of the invention the purpose of this is to act as a positioning means, its main object being to ensure the most perfect sealing-tightness possible between the inside and the outside of the reactor. Furthermore, this compression gland may be advantageously replaced by a simpler means of positioning sheaths such as for example simple washers of refractory material.

Figure 3A:
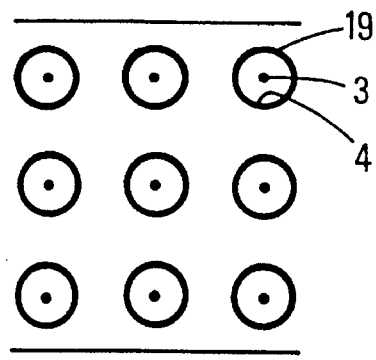
FIGS. 3A, 3B, 3C and 4A, 4B and 4C show a longitudinal section through various modules of the furnace construction.
Figure 3B:
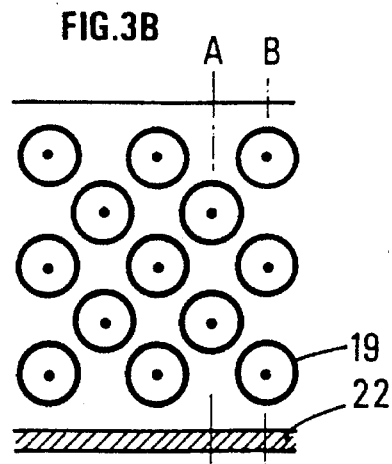
Figure 3C:
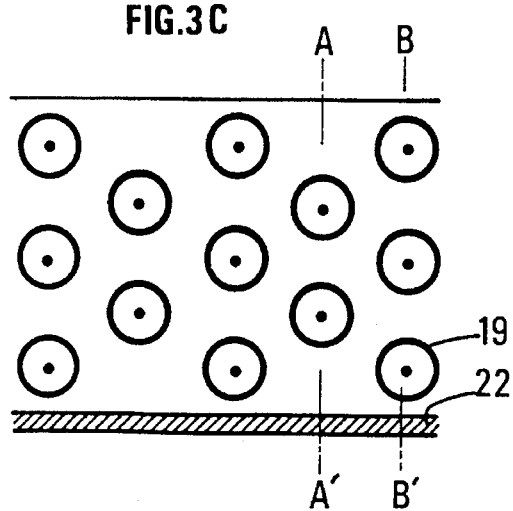
Figure 4A:
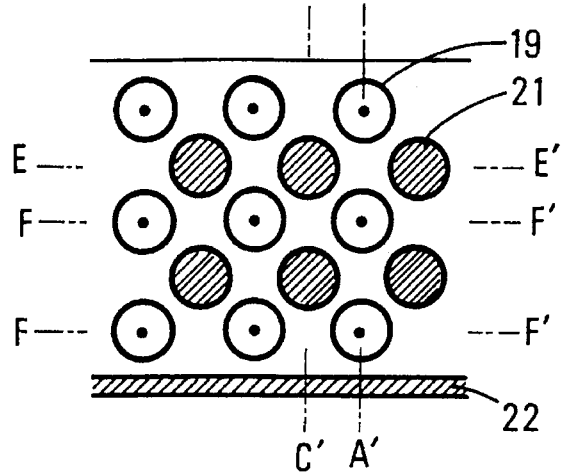
Figure 4B:
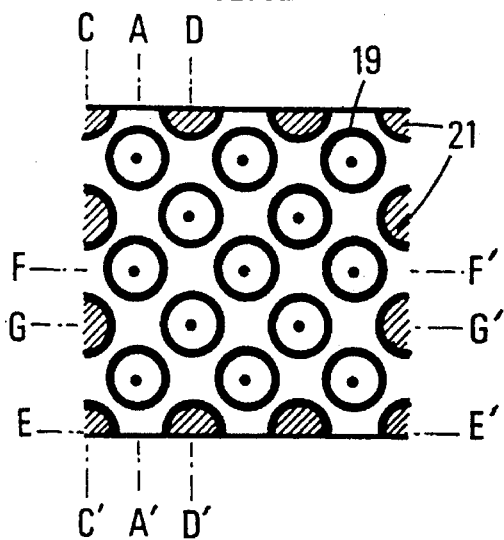

Thus, there are a certain number of heating resistors which are sheathed in walls, for example in ceramic material, in successive horizontal rows, these rows preferably being so aligned that, on the lateral walls of the furnace, they form a cluster of square or rectangular configuration. A casing (11) from which only the ends of the resistors and/or their electricity supply (6) projects, is traversed by a flow of gas containing hydrogen. FIGS. 3A, 3B, 3C, 4A, 4B and 4C diagrammatically show a longitudinal section through six types of modules which can be used for constructing the pyrolysis furnace according to the invention, the drawings showing a plane at right-angles to the axis of the elements. In the case of FIGS. 3A, 3B, 3C, these modules only comprise heating elements (19). In the case of FIGS. 4A, 4B ad 4C, these modules comprise heating elements (19) and pseudo heating elements (21). Each module will more often than not comprise from 2 to 30 and preferably 5 to 15 of these elements. Each module will normally comprise from 1 to 30 and most often from 5 to 11 heating elements.

The module shown diagrammatically in FIG. 3A has three transverse rows of heating elements. By association of modules of this type in a direction at right-angles to the transverse rows (that is to say parallel with the direction of flow of the gases), it will be possible to form a longitudinal zone comprising three layers of heating elements. It is similarly possible to associate modules of this type in accordance with two perpendicular directions and form a longitudinal zone comprising for example six layers of heating elements if the modules have been associated two-by-two in the direction at right-angles to the three transverse rows. The module shown diagrammatically in this FIG. 3A consists of elementary units each comprising one transverse row of three heating elements. In horizontal projection, the constituent elements of this module form a cluster of square configuration.

The module shown diagrammatically in FIG. 3B comprises five transverse rows of heating elements. This module is formed by transverse rows AA' comprising three heating elements separated from one another by transverse rows BB' of two heating elements. The constituent elements of this module, in horizontal projection, form a cluster of triangular configuration. The module shown diagrammatically in this FIG. 3B consists of elementary units each comprising two transverse rows, one of three heating elements and the next one of two heating elements. This module further comprises a refractory wall (22).

The module shown diagrammatically in FIG. 3C has five transverse rows of heating elements. This module only differs from that shown diagrammatically in FIG. 3B by the fact that the oblique distance between these elements is equal to the distance between these elements in the transverse direction and the distance in the direction of circulation of the gases between the elements is greater than the distance in the transverse direction.

The use of modules such as those shown diagrammatically in FIG. 3B and those shown diagrammatically in FIG. 3C having a geometry in quincunx with elements situated at a distance p from one another in the direction of flow of the gases and transversely and at an oblique distance (according to an axis substantially at 45° to the axis AA' of the transverse rows), p/2 in the case of the module shown diagrammatically in FIG. 3B and p in the case of the shown diagrammatically in FIG. 3C, makes it possible to create zones of constant velocity for the gases (module according to FIG. 3B) and zones of variable velocity for the gases (module according to FIG. 3C).

The module shown diagrammatically in FIG. 4A comprises three transverse rows AA' of heating elements and three transverse rows CC' of pseudo heating elements. By association of modules of this type according to a direction at right-angles to the transverse rows (that is to say parallel with the direction of gas flow), it is possible to form a longitudinal zone comprising layers FF' of heating elements and layers EE' of pseudo heating elements. The module shown diagrammatically in this FIG. 4A is formed by elementary units each comprising two transverse rows, one of three heating elements and the following one of two pseudo heating elements.

The module shown diagrammatically in FIG. 4B comprises seven transverse rows of elements: three transverse rows AA' of heating elements, two transverse rows CC' of pseudo heating elements and two transverse rows DD' comprising heating elements and pseudo heating elements. By association of modules of this type according to a direction at right-angles to the transverse rows (that is to say parallel with the direction of gas flow) and according to a direction parallel with these transverse rows, it is possible to form a longitudinal zone comprising layers FF' of heating elements, layers EE' of pseudo heating elements and layers GG' comprising heating elements and pseudo heating elements. This module comprises substantially cylindrical heating elements and the pseudo heating elements situated on the periphery of the module (on the sides of the module) are solid elements which according to their position are substantially in the form of a half-cylinder or substantially in the form of a quarter of a cylinder, so that by juxtaposition of the modules, pseudo elements are formed which are substantially cylindrical and which have a cross-section the area of which is substantially equal to that of the cross-section of the heating elements, or semi-cylindrical for those which are close to the walls of the longitudinal zone.

Figure 4C:
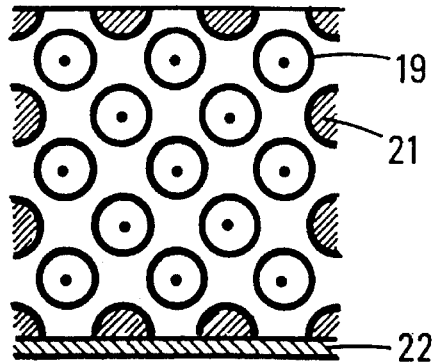

The module shown diagrammatically in FIG. 4C only differs from that shown in 4B by the fact that it also comprises a refractory wall 22.

The association of modules of different types is entirely possible. Thus, for example, in the case of the choice of a geometry where the elements are in quincunx and form a longitudinal zone, it is possible to associate modules such as those shown diagrammatically in FIGS. 3B and 3C.

EXAMPLE 1

An indirect quenching horizontal reactor is used which has a total length of 6.1 m and a rectangular cross-section of 1.4×2.89 m. The means of heating this reactor consist of hairpin-form electric resistors of KANTHAL make, of molybdenum bisilicide ($MoSi_2$) of the SUPERKANTHAL type; these resistors are enclosed by ceramic sheaths disposed concentrically in relation to the centre of the circle embracing the resistors.

These sheaths are of silicon carbide produced by NORTON company. They are of the KRYSTON type and have an open porosity of 15% by volume. Closed at one end, each sheath encloses two hairpin resistors (FIG. 1B). These sheaths are disposed at right-angles to the direction of circulation of the charge (vertically) in parallel layers, and in perpendicular projection they form a cluster of square configuration. The length of each arm of the hairpin of the electrical resistor is 1.4 m and its diameter is 9 mm. The ceramic sheaths are 1.4 m long, their outside diameter is 150 mm and their inside diameter is 130 mm; the distance separating two adjacent sheaths is 10 mm.

The first part of the heating zone, 3.7 m long, comprises 18 layers of resistors, each layer comprising 23 sheaths; in this zone, the charge which is preheated to 800° C., is raised to 1200° C. This zone is regulated thermally by means of thermocouples disposed in the spaces in which the charge circulates.

The second part of the heating zone, adjacent to the first part, is 2.4 m long; it consists of 18 layers of 15 sheaths, disposed in the same way as in the first part of the heating zone. This zone is constituted by 5 heating sections which are independently regulated, which make it possible to maintain the temperature in this zone at 1200° C. plus or minus 10° C.

The effluent gases are cooled in a first stage to 800° C. by indirect exchange with the gases of the charge; other temperature exchangers then make it possible to lower their temperature to approx. 300° C.

Used as a charge is methane diluted with hydrogen in a ratio of 1:1 by volume. This mixture is preheated to 800° C. and cracked in the above-described reactor. The absolute pressure of the gas mixture in the reactor is maintained substantially constant and equal to 0.125 MPa. Substantially pure hydrogen is introduced into the resistor space in order to obtain and maintain in this space an absolute pressure which is substantially constant and equal to 0.130 MPa.

After cooling to ambient temperature, for 200 moles of equivolumic mixture of methane and hydrogen, the following quantities of principal products are obtained:

| PRODUCTS | QUANTITIES |
|---|---|
| $H_2$ | 143 moles |
| $CH_4$ | 70 moles |
| $C_2H_2$ | 6 moles |
| $C_2H4$ | 4 moles |
| benzene | 0.75 moles |
| coke | 54 grams |

EXAMPLE 2

An indirect quenching horizontal reactor is used which has a total length of 4.31 m with a rectangular cross-section of 1.4×2.94 m. The means of heating consist of hairpin-shape electrical resistors of KANTHAL make, of molybdenum bisilicide ($MoSi_2$) of the SUPERKANTHAL type; these resistors are enclosed in ceramic sheaths disposed concentrically in relation to the centre of the circle embracing the resistors.

These sheaths are of silicon carbide produced by NORTON company. They are of the KRYSTON type and have an open porosity of 15% by volume. Closed at one end, each sheath encloses two hairpin resistors (FIG. 1B). These sheaths are disposed at right-angles to the direction of circulation of the charge (vertically) in parallel layers and in perpendicular projection they form a cluster of square configuration. The length of each arm of the hairpin of the electrical resistance measures 1.4 m and its diameter is 9 mm. The ceramic sheaths are 1.4 m long. Their outside diameter is 150 mm and their inside diameter 130 mm; the distances Eg and Et (FIG. 1A) separating two adjacent sheaths are 10 mm. The reactor comprises three longitudinal zones each comprising 6 layers of heating elements separated by a wall of electrically fused alumina-based refractory cement. The distance Ee (FIG. 1A) between the sheaths and the wall or size of the passages is 10 mm. The walls have, at their thinnest part, a thickness Ep (FIG. 1A) of 15 mm. Thus, the reactor comprises 18 layers of 27 heating elements and 2 walls.

The first part of the heating zone, 1.75 m long, comprises 18 layers of resistors, each layer comprising 11 sheaths; in this zone, the charge preheated to 1000° C. is raised to 1200° C. This zone is regulated thermally by means of thermocouples disposed in the spaces in which the charge circulates. The second part of the heating zone adjacent to the said first part is 2.56 m long; it is constituted by 18 layers of 16 sheaths disposed in the same way as in the first part of the heating zone. This zone is constituted by three heating sections which are independently regulated, making it possible to maintain the temperature in this zone at 1200° C. plus or minus 10° C.

The effluent gases are cooled in a first stage to 800° C. by indirect exchange with the gases of the charge; other temperature exchangers make it possible then to lower their temperature to approx. 300° C.

Used as a charge is methane diluted with hydrogen in a volumetric ratio of 1:1. This mixture is preheated to 1000° C. and cracked in the above-mentioned reactor. The absolute pressure of the gaseous mixture in the reactor is maintained substantially constant and is equal to 0.125 MPa. Substantially pure hydrogen is introduced into the resistor space in order to obtain and maintain in this space a substantially constant absolute pressure equal to 0.130 MPa. After cooling to ambient temperature, per 200 moles of equivolumic mixture of methane and hydrogen, the following quantities of principal products are obtained:

| PRODUCTS | QUANTITIES |
|---|---|
| $H_2$ | 142.5 moles |
| $CH_4$ | 70 moles |
| $C_2H_2$ | 6.3 moles |
| $C_2H_4$ | 4 moles |
| benzene | 0.74 moles |
| coke | 50 grams |

We claim:

1. An apparatus comprising a reactor of elongated shape, comprising a square or rectangular cross-section and a longitudinal axis, said reactor having a first end, a second end, inlet means at said first end for supplying a gaseous mixture, outlet means at said second end for discharging effluent, and means for supplying a cooling medium, said reactor further comprising at least one longitudinal zone between two walls one of refractory material adjacent said first end, at least one of said walls being disposed between outside walls of said reactor wherein said two refractory walls are substantially parallel to each other and substantially parallel to said axis of said reactor, said at least one longitudinal zone comprising a plurality of elements disposed in at least two layers, said layers being substantially parallel to each other, and substantially parallel to said axis of said reactor, wherein said elements in at least one of said layers comprises a series of sheaths inside which are electric heating means, thereby forming a series of heating elements, said elements in at least two layers being positioned to define passages for circulation of gas between said elements, between said layers of elements, and/or between said elements and walls, whereby said electric heating means and said sheaths are capable of heating said passages in successive independent sections which are substantially perpendicular to said axis of said reactor, each of said sections comprising at least one transverse row of elements, said reactor further comprising means for automatic control and modulation of heating connected to said electric heating means, and said reactor further comprising, adjacent said second end, means for cooling effluent connected to said means for supplying cooling medium.

2. An apparatus according to claim 1, wherein:

each longitudinal zone is formed by juxtaposition of a series of constituent modules of square or rectangular cross-section, each module comprising at least two elements forming a transverse row, at least one of said elements being formed by a sheath inside which electric heating means is provided and constitutes a heating element, said elements being disposed to define passages for circulation of gas between said elements and/or between said elements and said walls of said zone, and said modules being juxtaposed, whereby said elements form at least two layers, substantially parallel to each other and substantially parallel with said axis of said reactor, said layers being positioned between two walls of refractory material which are substantially parallel other and substantially parallel with said axis of said reactor.

3. An apparatus according to claim 2, wherein said constituent modules comprise at least two transverse rows of two or three heating elements disposed so that juxtaposition of said modules provides at least two layers of heating elements, said layers being perpendicular to said axis of said reactor and said elements forming in transverse projection a cluster of elements of triangular, square, or rectangular configuration.

4. An apparatus according to claim 2, wherein said constituent modules comprise at least two transverse rows, of which at least one is formed by heating elements and of which at least one other, contiguous upon a row of said heating elements, is formed by pseudo heating elements of refractory material, said elements being disposed whereby juxtaposition of said modules provides at least two layers of elements, said layers being perpendicular to said axis of said reactor and said elements forming in transverse projection a cluster of elements of triangular, square, or rectangular configuration.

5. An apparatus according to claim 4, wherein said constituent module comprises pseudo heating elements on its periphery, said pseudo heating elements having a cross-section whereby, as a result of juxtaposition of said modules, said pseudo heating elements situated at the edge of said modules form pseudo elements having substantially the same cross-section as said heating elements, said pseudo heating elements positioned on a single edge of said module having a cross-section equal to approximately half the cross-section of said heating elements and said pseudo heating elements positioned on two edges of said module having a cross-section equal to approximately one-quarter the cross-section of said heating elements.

6. An apparatus according to claim 1, wherein said reactor comprises at least two of said longitudinal zones formed by juxtaposition in the longitudinal direction and, in the transverse direction, said longitudinal zones are each a series of modules, said modules comprising at least one longitudinal wall of refractory material.

7. An apparatus according to claim 1, wherein each wall of refractory material separating two adjacent longitudinal zones comprises at least one means permitting balancing of pressures between said two adjacent longitudinal zones.

8. An apparatus according to claim 1, wherein: said elements comprise heating elements and pseudo heating elements.

* * * * *